(12) United States Patent
Wenzel (10) Patent No.: US 9,334,796 B2
(45) Date of Patent: May 10, 2016

(54) COAL-TO-LIQUID SYSTEMS AND METHODS

(71) Applicant: SAGA FUEL SYSTEMS, INC., Sparta, NJ (US)

(72) Inventor: Deborah Wenzel, Sparta, NJ (US)

(73) Assignee: SAGA FUEL SYSTEMS, INC., Sparta, NJ (US)

( * ) Notice: Subject to any disclaimer, the term of this patent is extended or adjusted under 35 U.S.C. 154(b) by 92 days.

(21) Appl. No.: 14/456,575

(22) Filed: Aug. 11, 2014

(65) Prior Publication Data

US 2014/0345546 A1 Nov. 27, 2014

Related U.S. Application Data

(63) Continuation of application No. 12/807,668, filed on Sep. 10, 2010, now Pat. No. 8,822,553.

(60) Provisional application No. 61/276,391, filed on Sep. 10, 2009.

(51) Int. Cl.
| | | |
|---|---|---|
| *C07C 1/04* | (2006.01) | |
| *F02B 63/04* | (2006.01) | |
| *C01B 3/02* | (2006.01) | |
| *C10L 1/182* | (2006.01) | |

(52) U.S. Cl.
CPC . *F02B 63/04* (2013.01); *C01B 3/02* (2013.01); *C07C 1/04* (2013.01); *C07C 1/0485* (2013.01); *C10L 1/1824* (2013.01)

(58) Field of Classification Search
CPC ........................................................ C07C 1/04
See application file for complete search history.

(56) References Cited

U.S. PATENT DOCUMENTS

| | | |
|---|---|---|
| 6,946,008 B2 | 9/2005 | Wenzel |
| 8,383,870 B2 * | 2/2013 | Knight .................... F01K 13/00 48/197 R |
| 8,822,553 B1 | 9/2014 | Wenzel |
| 2008/0256861 A1 * | 10/2008 | Van den Berg .......... C10J 3/485 48/210 |

* cited by examiner

*Primary Examiner* — Randy Boyer
(74) *Attorney, Agent, or Firm* — Wilson Sonsini Goodrich & Rosati (57) ABSTRACT

A Coal-to-Liquid Fuels production process by which carbon dioxide ($CO_2$) exhaust by-products are significantly reduced, if not eliminated, through a system comprising the generation of a first hydrogen ($H_2$) product and carbon from coal and generating carbon monoxide (CO) by reacting the Carbon (C) with $CO_2$. A second hydrogen ($H_2$) product is generated through catalyzation of water, methane reformation, electrolysis of water, or other reaction processes. Carbon monoxide (CO) is reacted with the first and second hydrogen ($H_2$) products to form a first hydrocarbon group having Olefins. The first hydrocarbon group, as Olefins, are further reacted to form C1-40 alcohols, Kerosene, Gasoline, Diesel Fuel, and Jet Fuel, and combinations thereof. At least a portion of the finished fuel blends are optionally used to generate electricity for use in the fuels production process or for distribution to an external power grid. Kerosene, Gasoline, Diesel Fuel, and/or Jet Fuel are optionally blended with C1-C40 alcohol combinations for most efficient utilization of all available Carbon and to improve combustion characteristics of the finished fuels.

16 Claims, 11 Drawing Sheets

COAL-TO-LIQUID SYSTEMS AND METHODS

CROSS-REFERENCE

This application is a continuation application of U.S. patent application Ser. No. 12/807,668, filed Sep. 10, 2010, which claims the benefit of U.S. Provisional Application No. 61/276,391, filed Sep. 10, 2009, each of which is entirely incorporated herein by reference.

BACKGROUND OF THE INVENTION

The currently-used prior art coal-to-liquid fuel production system is generally known as the Fischer-Tropsch coal-to-liquid (herein: FTCTL) fuel process. It is also generally known by those skilled in the art that, while the FTCTL process is chemically effective in producing liquid fuels from coal, the resulting tonnage of carbon dioxide exhaust by-product stream is severely detrimental to environmental air quality, and is a significant contributor to increased levels of $CO_2$ in the earth's atmosphere, which are known to also negatively impact global warming trends.

Additionally, finished fuels generally produced using the FTCTL system are currently constructed to most closely resemble fuel characteristic specifications associated with fossil-derived fuels as Kerosene, Gasoline, Diesel Fuel, and Jet Fuel, which fuels are known to burn at varying levels of efficiency, and are known to produce end-use exhaust by-products such as soot, $NO_x$, and fuel vapor contamination of the atmosphere.

The following stepwise descriptions of the FTCTL production system are intended to most concisely represent the core reactions relating to coal-to-liquids fuel production, and more specifically to outline the reactions especially relating to the problem of $CO_2$ exhaust and finished fuel blending streams, but are not intended to fully represent the entire spectrum of extreme industrial conditions required to produce liquid fuel from coal, or to describe every reaction that occurs in a coal-to-liquids production facility.

Step One of the FTCTL coal-to-liquids production process, is to combust raw coal in an ambient or oxygen-enriched atmosphere to yield heat for heat-reaction production processes, with residual byproducts such as slag and sulphur separated out and used as raw material in related but separate industries; and with gaseous Carbon Dioxide ($CO_2$) exhausted to the external atmosphere.

Step Two of the FTCTL process is to combust raw coal in a low-oxygen atmosphere to produce a gaseous mixture of Hydrogen ($H_2$) and Carbon Monoxide (CO), with the ratio of $H_2$:CO as approximately 0.8:1.

Step Three of the FTCTL process addresses the need to increase the $H_2$:CO ratio from 0.8:1 to 2:1—a requirement for successful hydrocarbon fuel production. This is accomplished by redirecting a portion of Carbon Monoxide (CO) produced in Step Two and catalyzing Carbon Monoxide (CO) with water ($H_2O$) and a metal (generally Nickel) to produce the necessary volume of Hydrogen ($H_2$). Hydrogen ($H_2$) is redirected to the fuels production stream, and $CO_2$ as by-product is exhausted to the external atmosphere.

Step Four of the FTCTL process further reacts the now hydrogen-enriched $H_2$:CO ratio 2:1 mixture to form waxy alcohols, or Olefins.

Step Five of the FTCTL process modifies the olefin stream to produce 'generic' hydrocarbon fuel, generally described as 'Kerosene.'

Step Six of the FTCTL process further reacts Kerosene in a fuel characteristic 'tailoring' process to yield finished fuels as Gasoline, Diesel Fuel, and Jet Fuel.

SUMMARY OF THE INVENTION

The present invention relates to a system of reaction processes, which system comprises:

Step One of the present invention is to combust raw coal in an ambient or oxygen-enriched atmosphere to yield heat for heat-reaction production processes, with residual byproducts such as slag and sulphur separated out and used as raw material in related but separate industries; however, in the present invention, gaseous Carbon Dioxide ($CO_2$) is captured and novelly re-directed for a second reaction with Carbon-black, or 'Coke' (C) to form gaseous Carbon Monoxide (CO), which is re-directed as an essential usable compound into the hydrocarbon fuel production stream.

Step Two of the present invention is novelly re-oriented (compared to the prior art which combusts raw coal in a low-Oxygen atmosphere to form CO) to pyrolize raw coal in a high-temperature no-oxygen environment to form carbon-black, or 'Coke' (C) which is then reacted with re-captured $CO_2$ (see above and below) to form Carbon Monoxide (CO), as an essential hydrocarbon fuel production compound.

Step Three of the present invention yields the additional hydrogen needed to form the hydrogen-rich $H_2$:CO 2:1 gaseous combination which is required for the formation of hydrocarbon fuel. In the present invention, however, hydrogen production processes can be optionally configured to include any one or combination of reactions, which reactions comprise the following below:

In an aspect, carbon monoxide (CO) is catalyzed with a metal and water to form usable Hydrogen ($H_2$), with carbon dioxide ($CO_2$) recaptured and reacted with carbon black, coke (C) as above, to form usable carbon monoxide (CO).

In another aspect, natural gas methane ($CH_4$), is reformed with steam to produce usable Hydrogen ($H_2$), with Carbon Dioxide ($CO_2$) recaptured and reacted with Carbon Black, Coke (C) as above, to form usable Carbon Monoxide (CO).

In another aspect, natural gas Methane ($CH_4$) is reacted with Oxygen ($O_2$) to form usable Hydrogen ($H_2$) and usable Carbon Monoxide (CO).

In another aspect, natural gas Methane ($CH_4$) is dry-reformed with a catalyst and Carbon Dioxide ($CO_2$) from Step One to form usable Hydrogen ($H_2$) and usable Carbon Monoxide (CO).

In another aspect, Heat from Step One is partially re-directed to form Steam, which Steam is used to drive Steam Turbines to form Electricity, which Electricity is used to electrolyze water ($H_2O$) for the production of usable Hydrogen ($H_2$) for the hydrocarbon fuels production stream, and optionally partially directed to an external electric power grid, and usable Oxygen ($O_2$) is recirculated to improve combustion reactions.

In another aspect, a portion of Olefins from Step Four of the total system are re-directed to produce C1-40 Alcohol side stream combinations, which Alcohols are blended with Kerosene from Step Five or with Diesel Fuel from Step Six of the total system to form a highly efficient, alcohol-rich fuel for combustion in Diesel Engines, which Engines produce Electricity for Electrolysis of water, as above; and $CO_2$, which is re-directed to react with Carbon-black, or 'Coke' (C), as above, to form usable Carbon Monoxide (CO).

In another aspect, any reaction or external source is used to provide usable Hydrogen ($H_2$); by-product Oxygen is re-circulated to improve combustion reactions within the system, and by-product Carbon Dioxide ($CO_2$) is re-directed to react with Carbon-black, or 'Coke' (C), to form usable Carbon Monoxide (CO).

Step Four of the present invention reacts the now hydrogen-enriched $H_2$:CO 2:1 mixture to form waxy alcohols, or Olefins, and can additionally re-direct a portion of the Olefin stream to produce C1-40 Alcohols, which Alcohols can be tailored for use as a finished product, or blended with Kerosene or Gasoline, Diesel Fuel or Jet Fuel to improve combustion characteristics of the total fuel.

Step Five of the present invention modifies either the entire or the remaining Olefin stream to produce 'generic' hydrocarbon fuel, generally described as 'Kerosene,' which Kerosene can be optionally additionally blended with C1-40 Alcohols, as above, to improve combustion characteristics of the Kerosene fuel.

Step Six of the present invention further reacts Kerosene in a fuel characteristic 'tailoring' process to yield finished fuels as Gasoline, Diesel Fuel, and Jet Fuel, which Fuels can be optionally additionally blended with C1-40 Alcohols, as above, to improve combustion characteristics of the Gasoline, Diesel Fuel, or Jet Fuel.

In another aspect, a portion of the Olefin stream is re-directed to produce C1-40 Alcohols, which Alcohols are tailored for blending with Kerosene or Gasoline, Diesel Fuel or Jet Fuel and are incorporated into the finished Kerosene, Gasoline, Diesel fuel and Jet Fuel to improve combustion characteristics of the total finished fuels, e.g. vapor contamination reduction, soot reduction, NOx reduction, and improved fuel efficiency.

In another aspect, Step Six of the present invention can be eliminated from the production process, so that the final fuel product is Kerosene which has been additionally blended with C1-40 Alcohols, as above, to improve combustion characteristics of the total Kerosene fuel, e.g. soot reduction and improved fuel efficiency.

In another aspect, Steps Five and Six of the present invention can be eliminated from the production process, yielding a final fuel product as C1-40 Alcohols, or variously blended C1-40 alcohols, which can be shipped to an external source for blending with Kerosene, Gasoline, Diesel Fuel, Jet fuel, Heating Oil, Marine Fuel, Heavier Distillate Fuels or Bunker Fuels to improve combustion characteristics of the total fuels.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The invention will be better understood from the Detailed Description of the Invention and from the appended drawings, which are meant to illustrate and not to limit the invention.

DETAILED DESCRIPTION OF THE INVENTION

The present invention generally relates to coal-to-liquid systems and methods, more particularly to systems and methods for generating liquid fuels and electricity from coal.

The present invention concerns a novel system for combining production processes so that these processes, when used as the methods for producing liquid fuel and electricity from coal, significantly reduce Carbon waste of the total system, Carbon Dioxide exhaust by-products, and improve total energy output of the fuels production system, compared to traditionally employed coal-to-liquid fuel and coal-to-electricity production methods.

By combining coal and steel industry-standard reaction processes in a new and novel stepwise progression, and optionally utilizing new and novel oleochemical blending processes for final fuel characterization, this inventive system makes it possible to re-direct by-product carbon dioxide ($CO_2$), which is generally detrimentally exhausted to the external atmosphere, to form a reaction with Carbon-black, or 'Coke' (C) to form a usable stream of Carbon Monoxide (CO). Additionally, other by-products naturally occurring in the coal-to-liquid production stream are optionally re-directed for superior final fuel blend processing to maximize the liquid utilization of all available Carbon, Hydrogen and Oxygen for best possible efficiency of the finished fuel.

Other elements of this new inventive system for producing liquid fuels and/or electricity from coal include several alternative possible hydrogen-yielding and alcohol-producing sub-processes that can be optionally singly or severally combined to yield best possible overall production system efficiency, depending on raw materials and industry processes regionally available in any given production facility location.

In preferable embodiments of the invention, methods are provided for producing liquid hydrocarbon fuels and electricity while minimizing, if not eliminating, the emission of by-product Carbon Dioxide ($CO_2$) exhaust. Finished fuels can be improved through enrichment using alcohols from the fuels production stream.

In a preferable embodiment, coal is combusted in an ambient or oxygen-enriched atmosphere to generate heat and Carbon Dioxide ($CO_2$). Carbon Dioxide ($CO_2$) is reacted with Carbon-black (C) to produce Carbon Monoxide (CO), which is introduced into the production stream for further reaction with Hydrogen ($H_2$) as a preliminary step in the production of finished hydrocarbon fuels.

In a preferable embodiment, raw coal is pyrolyzed in a high temperature no-oxygen environment to produce Carbon (C) and Hydrogen ($H_2$), defining a first $H_2$ product. Carbon (C) is reacted with $CO_2$ to form CO, which is reacted with the first $H_2$ product to form alkenes (such as olefins) in the fuel production process.

In a preferable embodiment, the mole ratio of $H_2$ and CO before final processing can be nearly 1-to-1, or 1-to-0.8. This deficiency in $H_2$ is eliminated by enriching the first $H_2$ product with a second $H_2$ product formed from the catalyzation of water, methane reformation, electrolysis of water, or other reaction processes, thereby forming the necessary additional Hydrogen ($H_2$) product for reaction in the fuels production processes of various embodiments of the invention.

In a preferable embodiment, $H_2O$ is dissociated into $H_2$ and Oxygen ($O_2$) via the electrolysis of $H_2O$. $O_2$ from the dissociation of water is redirected to the improvement of combustion reactions. The first and second $H_2$ products are combined and reacted in the fuels production process with CO (in a 2-to-1 $H_2$-to-CO mole ratio) to form a first hydrocarbon group comprising one or more hydrocarbons.

In a preferable embodiment, the first hydrocarbon group comprises one or more alkenes, $CH_2=CH(CH_2)_nCH_3$, wherein 'n' is an integer greater than or equal to 1.

Next, a portion of the first hydrocarbon group is converted to a second hydrocarbon group comprising one or more hydrocarbons. In a preferable embodiment, the second hydrocarbon group comprises one or more alkanes, $CH_3(CH_2)_mCH_3$, wherein 'm' is an integer greater than or equal to 1. In an embodiment, the second hydrocarbon group comprises kerosene. The second hydrocarbon group can be stored as a saleable product.

At least a portion of the second hydrocarbon group can be combined with one or more alcohols to form a fuel blend or mixture. In an embodiment, the one or more alcohols are formed from a portion of the first hydrocarbon group.

The fuel blend can be combusted in an electricity generator to produce electricity and Carbon Dioxide ($CO_2$) as byproduct. The electricity formed by the electricity generator can be used to generate $H_2$ and $O_2$ through the electrolysis of $H_2O$. A portion of the electricity formed by the electricity generator can be directed to an electricity storage unit, an external electrical grid, or both.

$O_2$ formed from the dissociation of $H_2O$ can be re-directed to improve combustion reactions of the fuel production system. $H_2$ formed from the dissociation of $H_2O$ is re-directed for reaction with CO.

In a preferable embodiment, $CO_2$ formed in the fuels production processes of embodiments of the invention can be catalytically reduced to CO. The CO thus formed can be combined with CO from coal for further reaction in the fuels production processes of embodiments.

In an embodiment, at least a portion of the fuel generated in the processes of embodiments of the invention can be used to generate electricity for converting coal to $H_2$ and Carbon. Electricity can be generated by combusting the fuel in an electrical generator, for example. In another embodiment of the invention, heat from Reaction 1 can be re-directed to produce steam for steam-turbine electricity generation.

During the production of electricity, a first nitrogen-containing compound (e.g., $NO_x$, wherein 'x' is number greater than or equal to 1) can be formed. In an embodiment, the first nitrogen-containing compound can be converted to a second nitrogen-containing compound, such as, e.g., $NH_3$. In an embodiment, the second nitrogen-containing compound can be stored for use as a saleable product. This advantageously reduces, if not eliminates, release of nitrogen-containing pollutants into the environment during the generation of electricity.

Figure 1:
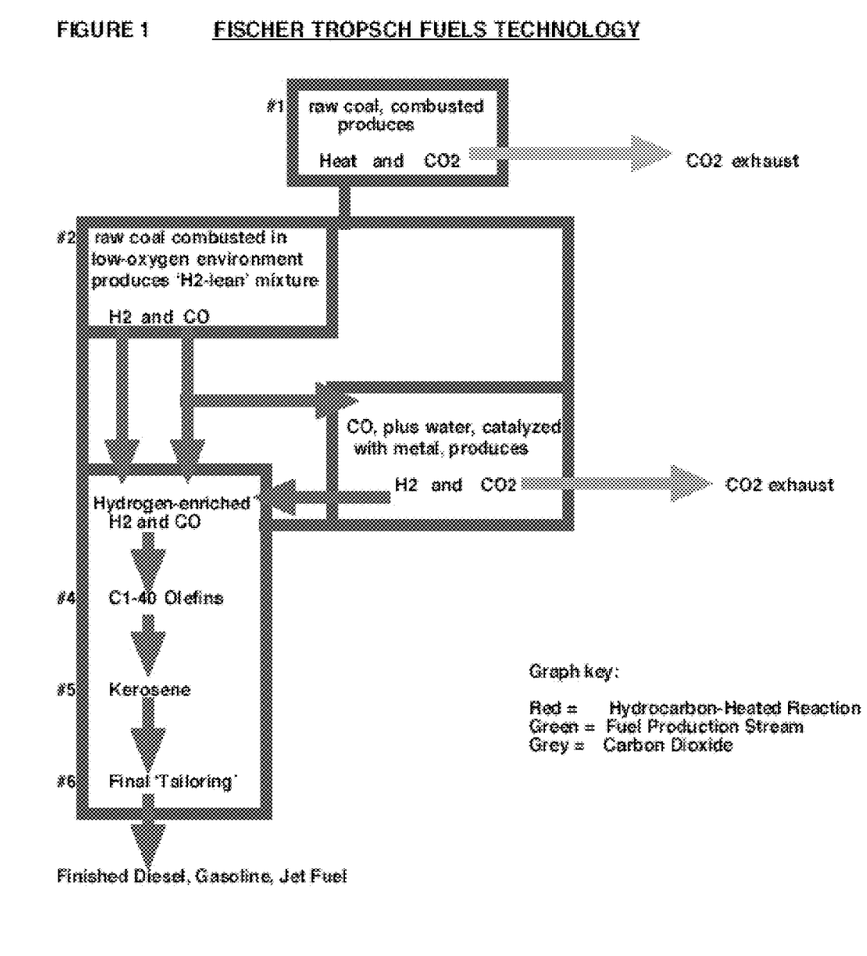
FIG. 1 shows a prior art coal-to-liquid process, generally known as the Fischer Tropsch coal-to-liquid fuel production process, in which by-product $CO_2$ is exhausted to the external atmosphere, in accordance with an embodiment of the invention.
Figure 2:
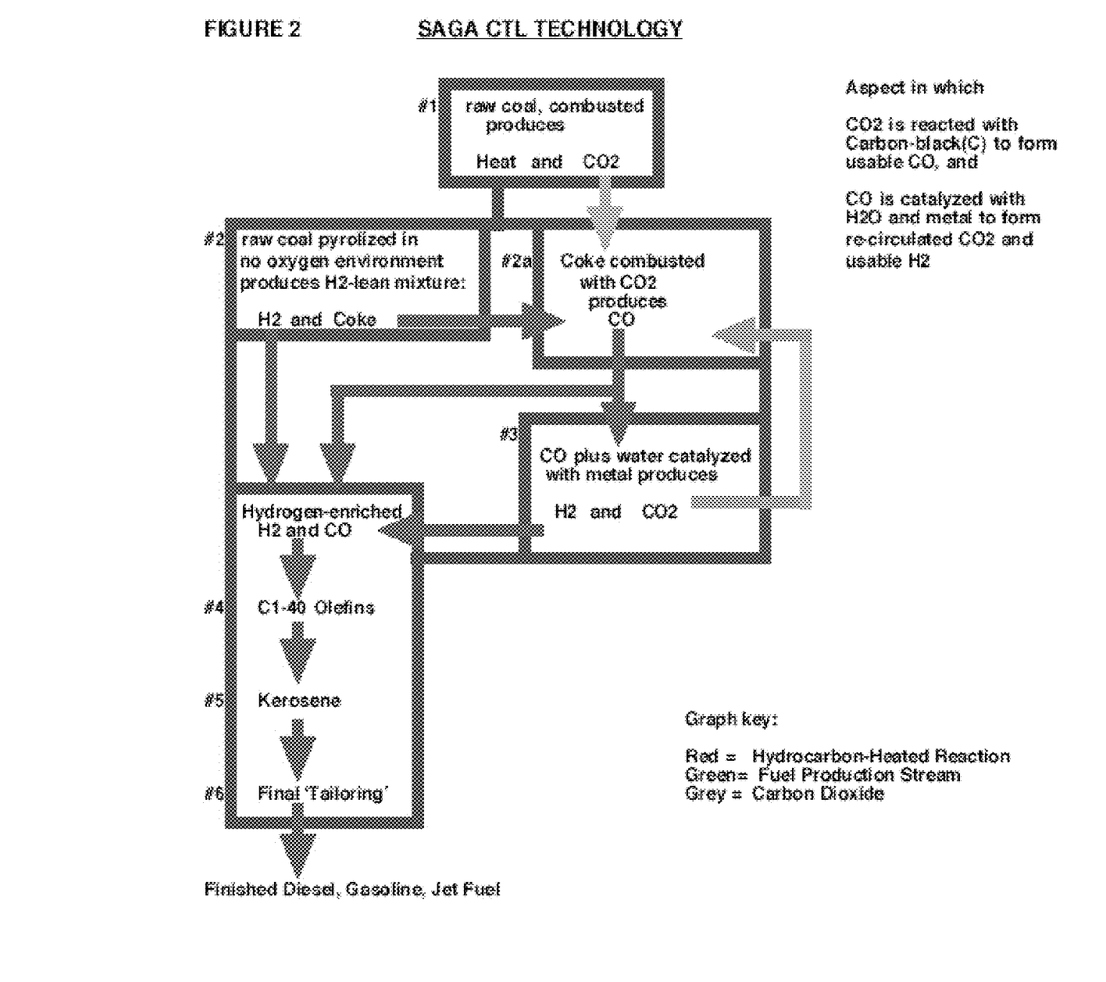
FIG. 2 shows a coal-to-liquid process in which Carbon Monoxide (CO) is catalyzed with a metal and water to form usable Hydrogen ($H_2$), with Carbon Dioxide ($CO_2$) recaptured and reacted with Carbon Black, Coke (C) as above, to form usable Carbon Monoxide (CO), in accordance with an embodiment of the invention.
Figure 3:
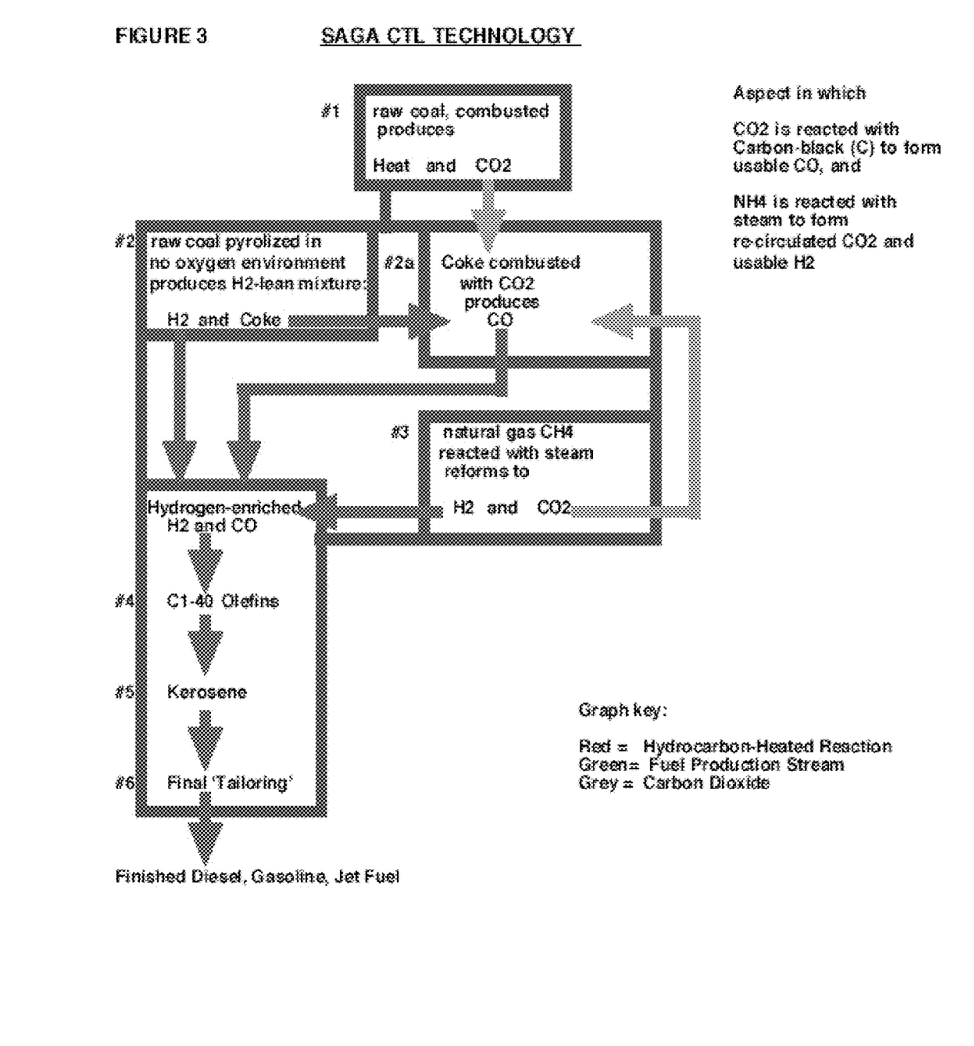
FIG. 3 shows a coal-to-liquid process in which natural gas Methane ($CH_4$), is reformed with steam to produce usable Hydrogen ($H_2$), with Carbon Dioxide ($CO_2$) recaptured and reacted with Carbon Black, Coke (C) as above, to form usable Carbon Monoxide (CO), in accordance with an embodiment of the invention.
Figure 4:
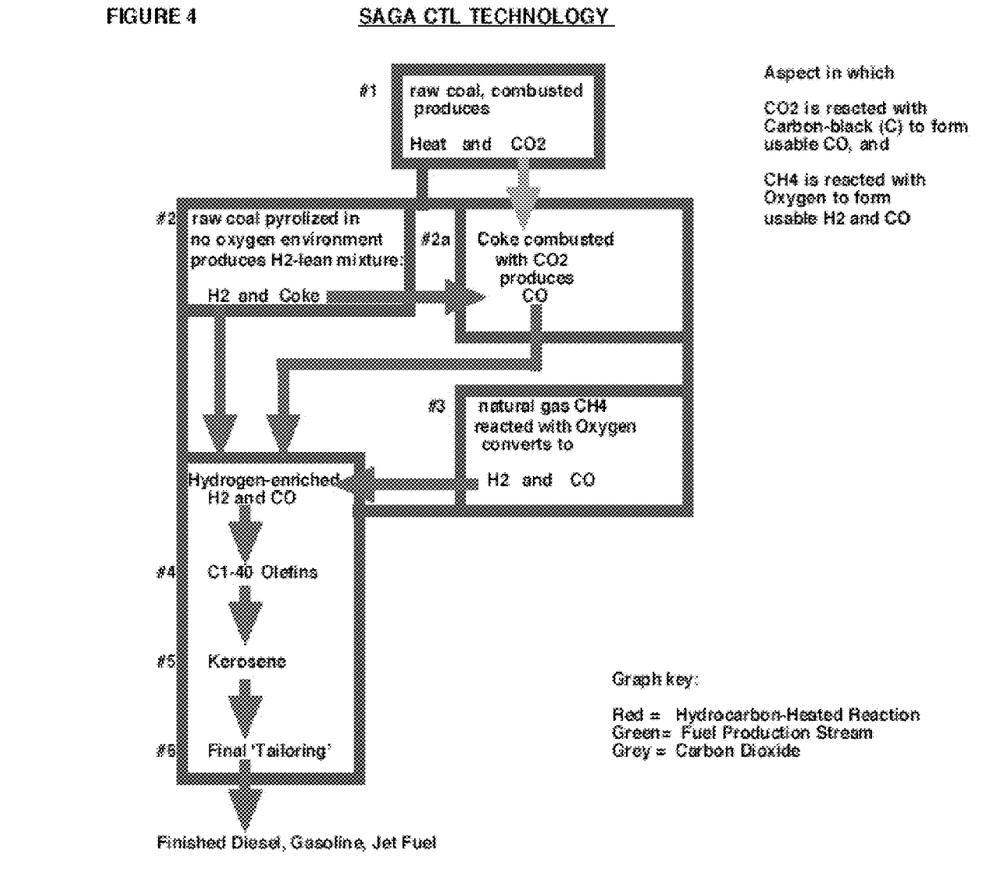
FIG. 4 shows a coal-to-liquid process in which natural gas Methane ($CH_4$) is reacted with Oxygen ($O_2$) to form usable Hydrogen ($H_2$) and usable Carbon Monoxide (CO), in accordance with an embodiment of the invention.
Figure 5:
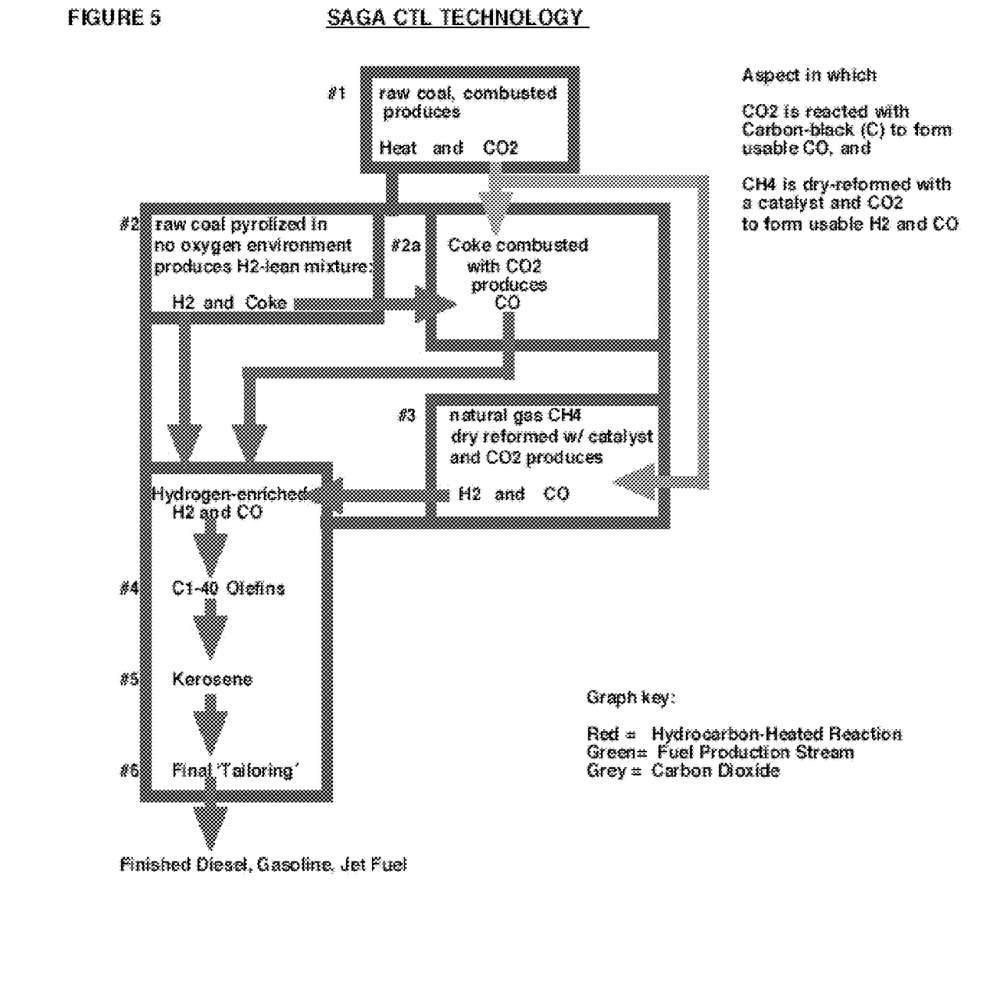
FIG. 5 shows a coal-to-liquid process in which natural gas Methane ($CH_4$) is dry-reformed with a catalyst and Carbon Dioxide ($CO_2$) from Step One to form usable Hydrogen ($H_2$) and usable Carbon Monoxide (CO), in accordance with an embodiment of the invention.

With reference to FIG. 1, a carbon-to-liquid (CTL) process for forming liquid hydrocarbons from coal is illustrated. In a first reaction (Reaction 1), coal is burned in Oxygen ($O_2$) to generate heat and $CO_2$. $CO_2$ is typically released into the atmosphere. In a second reaction (Reaction 2), coal is burned in low $O_2$ to generate CO and $H_2$ that can be in a 1 to 0.8 mole ratio. In a third reaction (Reaction 3), a fraction of CO formed from coal is reacted with $H_2O$ over a heterogeneous catalyst (e.g., Ni catalyst) to generate $H_2$ and $CO_2$. In a fourth reaction (Reaction 4), $H_2$ is combined with $H_2$ from coal and CO. In a preferable embodiment, $H_2$ is combined with $H_2$ from coal and CO to provide a nearly one-to-two mole ratio of CO and $H_2$, respectively. $CO_2$ is exhausted to the external environment. In a fifth reaction (Reaction 5), CO and $H_2$ are reacted in a Fischer-Tropsch (FTCTL) reaction to form one or more alkenes, $CH_2=CH(CH_2)_nCH_3$, wherein 'n' is an integer greater than or equal to 1. Next, in a sixth reaction (Reaction 6), a fraction of the one or more alkenes is reduced to one or more alkanes, $CH_3(CH_2)_mCH_3$, wherein 'm' is an integer greater than or equal to 1. The integer 'm' can be tailored to particular applications. For instance, the one or more alkanes can be tailored for use as jet fuel, diesel fuel, or gasoline.

Improved Methods for Forming Fuel

Figure 6:
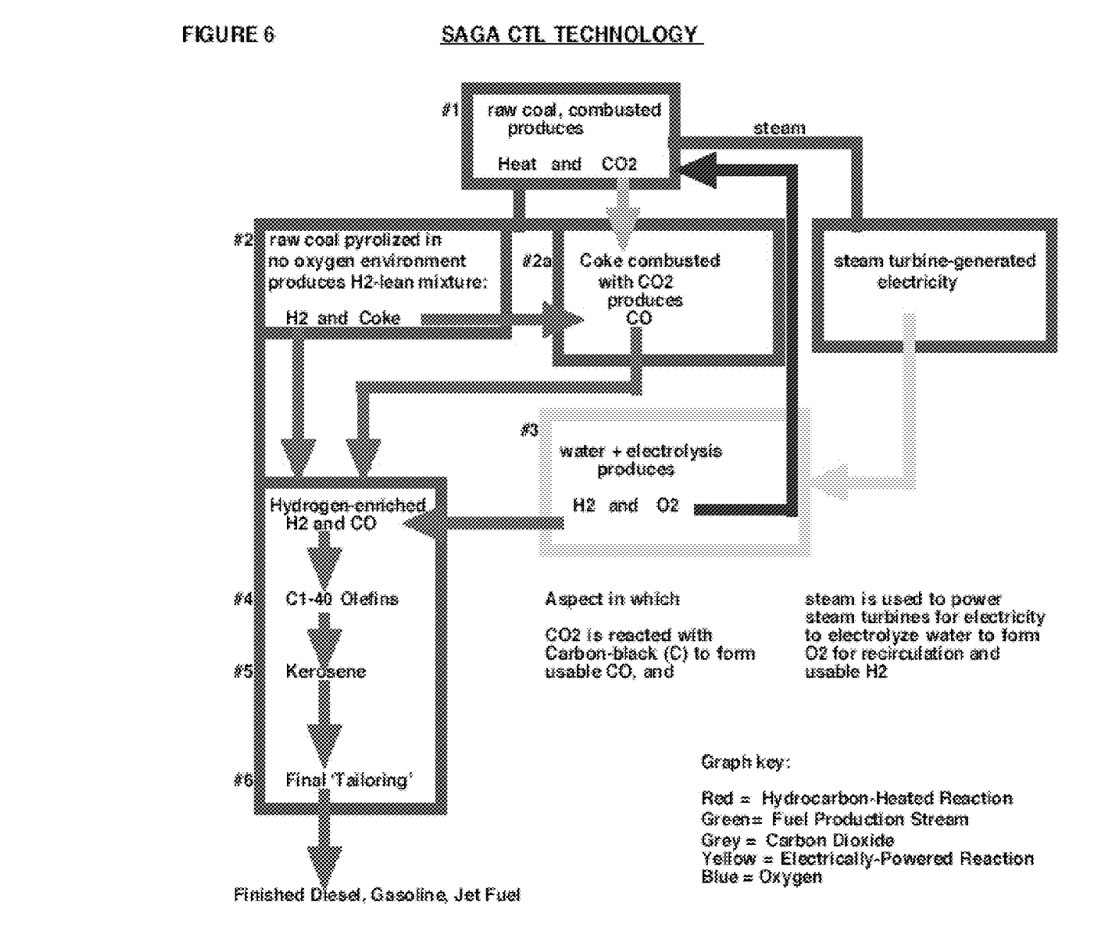
FIG. 6 shows a coal-to-liquid process in which Heat from Step One is partially re-directed to form Steam, which Steam is used to drive Steam Turbines to form Electricity, which Electricity is used to electrolyze water ($H_2O$) for the production of usable Hydrogen ($H_2$) for the hydrocarbon fuel production stream, and usable Oxygen ($O_2$) which is recirculated to improve combustion reactions, in accordance with an embodiment of the invention.

With reference to FIG. 6, in a first reaction (Reaction 1), coal is burned in an $O_2$ atmosphere to form $CO_2$ and heat. In a second reaction (Reaction2), the heat produced in the first reaction is used to generate $H_2$ and carbon from coal. In an embodiment, the second reaction is carried out in a substantially Oxygen-free environment. The $H_2$ from coal defines a first $H_2$ product. In an embodiment, the mole ratio of $H_2$ and CO (i.e., $nH_2/nCO$) is less than or equal to about 1, or less than or equal to about 0.9, or less than or equal to about 0.8.

The $CO_2$ formed in the first reaction is directed to a reaction chamber for reacting $CO_2$ with carbon to form CO. The CO is directed to the fuels production process.

With continued reference to FIG. 6, in a third reaction (Reaction 2a), any $CO_2$ produced in Reaction 1 and carbon formed in Reaction 2 are reacted to form CO, which is directed to the fuels production process. In an embodiment, any shortage of $H_2$ can be met by dissociating $H_2O$ into $H_2$ and $O_2$ (Reaction 3). The $H_2$ from the dissociation of water defines a second $H_2$ product. In an embodiment, water is dissociated into $H_2$ and $O_2$ via electrolysis.

With continued reference to FIG. 6, the electrical energy for electrolysis can be provided from a steam-turbine electrical generator (see below). In a preferable embodiment, the heat required to produce steam for steam-turbine electricity generation is re-directed from a portion of the heat produced in Reaction 1 in which coal is burned in an $O_2$ atmosphere to form $CO_2$ and heat. The $CO_2$ formed in the first reaction is directed to a reaction chamber for reacting $CO_2$ with carbon to form CO. The CO is directed to the fuels production process.

In one embodiment, $O_2$ formed upon the dissociation of $H_2O$ can be emitted to the external environment. In another embodiment, $O_2$ formed upon the dissociation of $H_2O$ can be reacted with coal in the first reaction.

Figure 7:
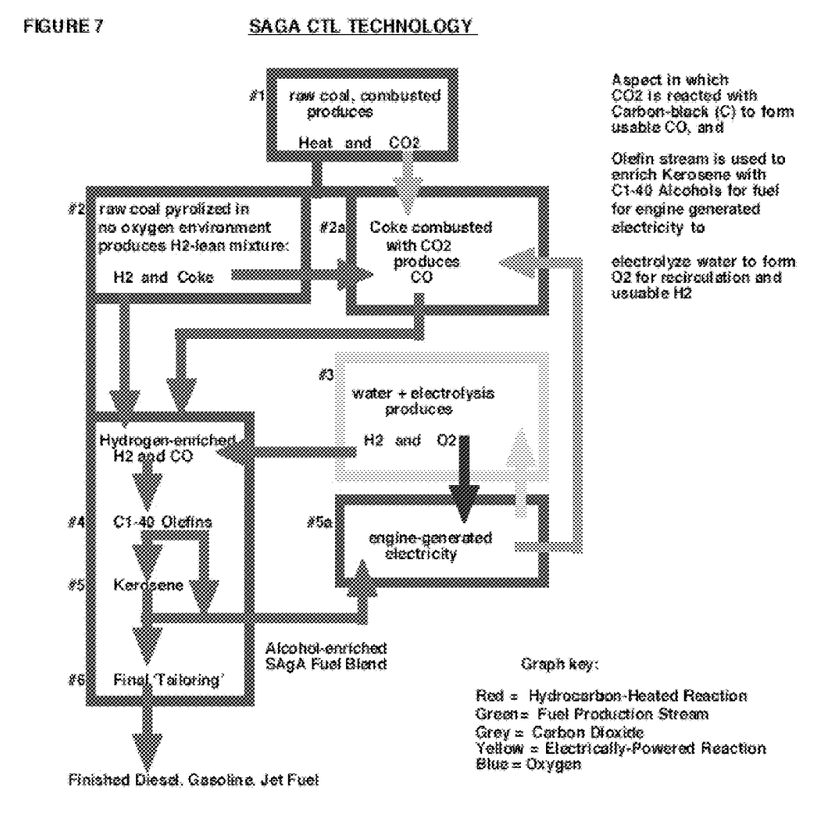
FIG. 7 shows a coal-to-liquid process in which a portion of Olefins from Step Four of the total system are re-directed to produce C1-40 Alcohol side stream combinations, which Alcohols are blended with Kerosene from Step Five or with Diesel Fuel from Step Six of the total system to form a highly efficient, alcohol-rich fuel for combustion in Diesel Engines, which Engines produce Electricity for Electrolysis of water, as described above, and is optionally partially or wholly directed to an external electric power grid; and $CO_2$, which is re-directed to react with Carbon-black, or 'Coke' (C), as above, to form usable carbon monoxide (CO), in accordance with an embodiment of the invention.

With reference to FIG. 7, in a first reaction (Reaction 1), coal is burned in an $O_2$ atmosphere to form $CO_2$. The first reaction is an exothermic reaction, generating heat. In a second reaction (Reaction 2), the heat produced in the first reaction is used to generate $H_2$ and Carbon from coal. In an embodiment, the second reaction includes extracting $H_2$ and carbon from coal. In an embodiment, the second reaction is carried out in a substantially oxygen-free environment. The $H_2$ from coal defines a first $H_2$ product. In an embodiment, the mole ratio of $H_2$ and CO (i.e., $nH_2/nCO$) is less than or equal to about 1, or less than or equal to about 0.9, or less than or equal to about 0.8.

Figure 8:
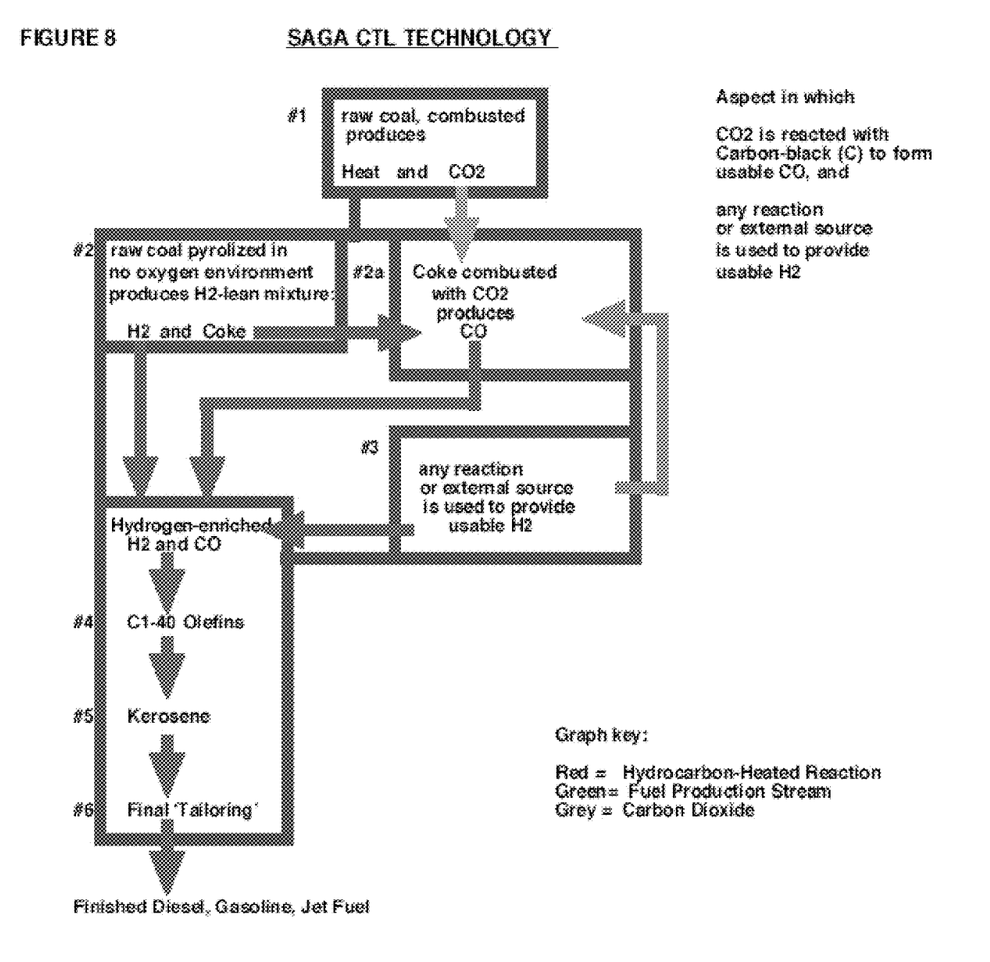
FIG. 8 shows a coal-to-liquid process in which any reaction or external source is used to provide usable Hydrogen ($H_2$), any by-product as Oxygen is re-circulated to improve combustion reactions within the system, and any by-product Carbon Dioxide ($CO_2$) is re-directed to react with Carbon-black, or 'Coke' (C), to form usable Carbon Monoxide (CO), in accordance with an embodiment of the invention.
Figure 9:
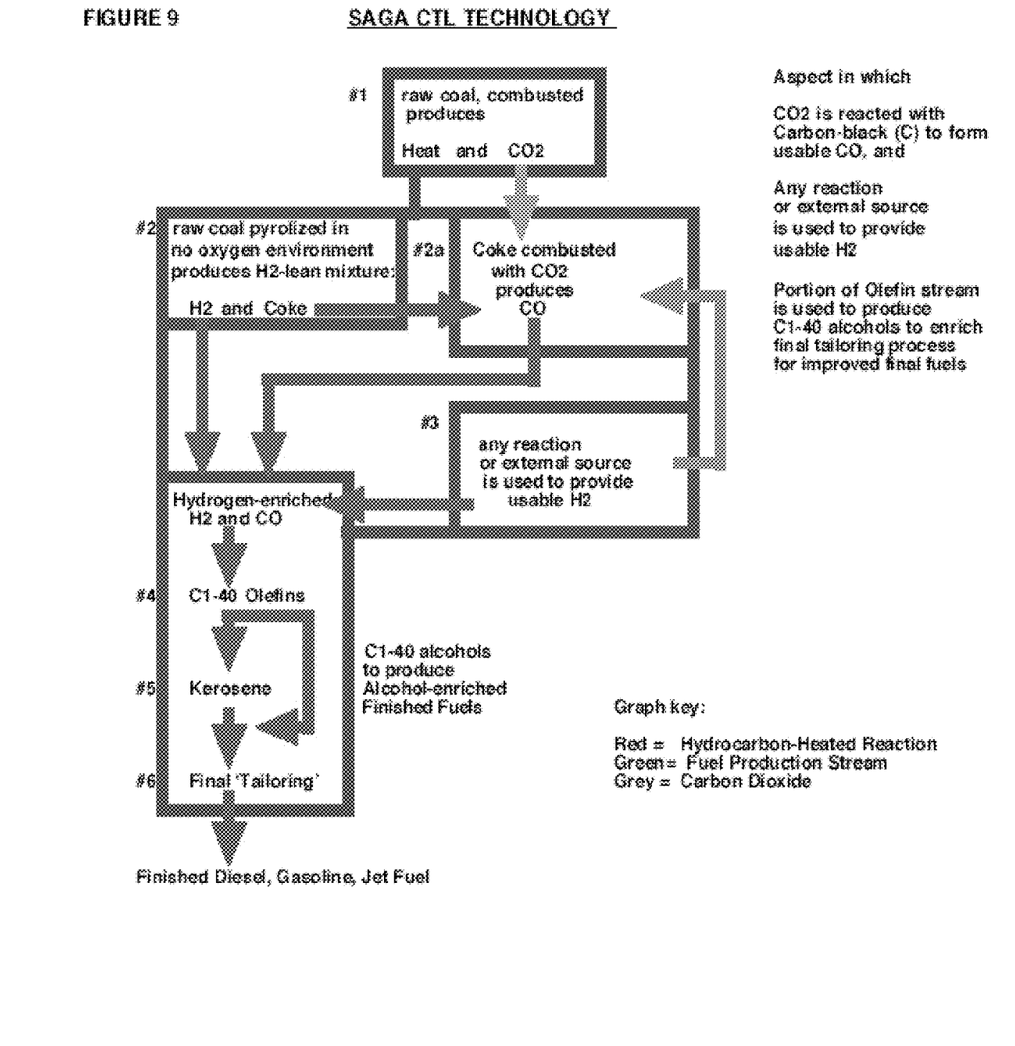
FIG. 9 shows a coal-to-liquid process in which any reaction or external source is used to provide usable Hydrogen ($H_2$), and a portion of the Olefin stream is re-directed to produce C1-40 Alcohols, which Alcohols are tailored for blending with Kerosene or Gasoline, Diesel Fuel or Jet Fuel and are incorporated into the finished fuels to improve combustion characteristics of the total finished fuels, e.g. vapor contamination reduction, soot reduction, $NO_x$ reduction, and improved fuel efficiency, in accordance with an embodiment of the invention.
Figure 10:
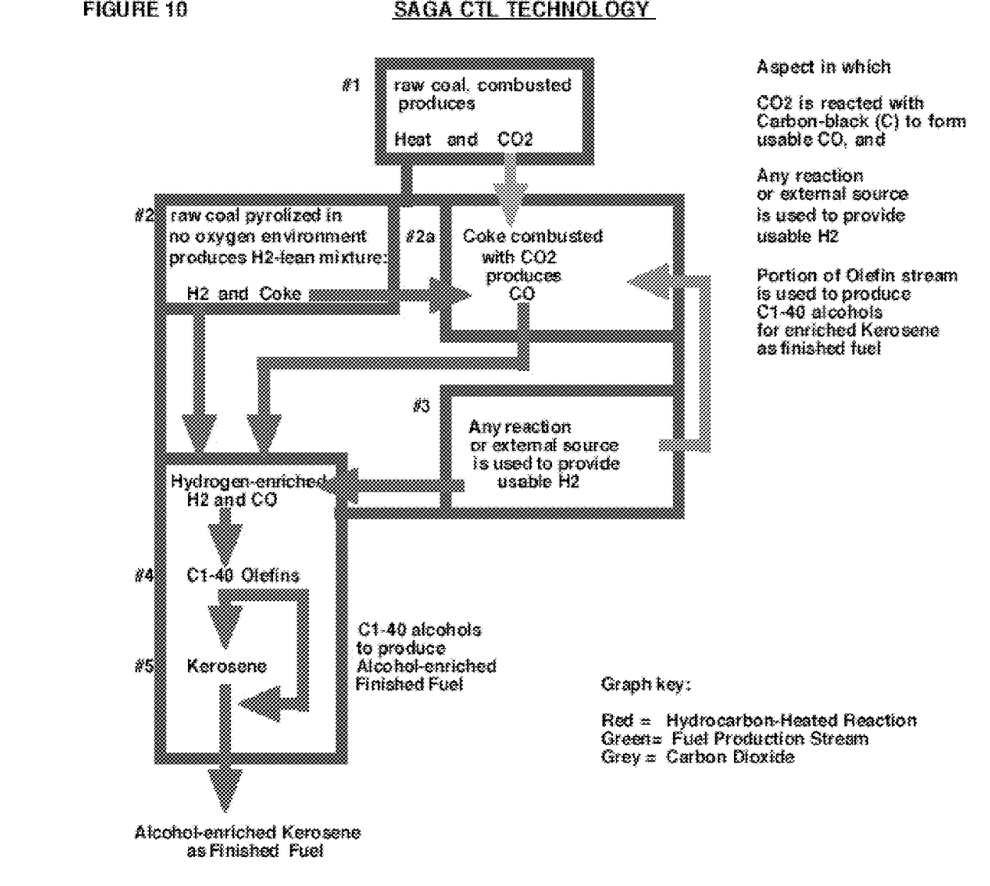
FIG. 10 shows a coal-to-liquid process in which any reaction or external source is used to provide usable Hydrogen ($H_2$), and a portion of the Olefin stream is re-directed to produce C1-40 Alcohols, which Alcohols are tailored for blending with Kerosene, to improve combustion characteristics of the total Kerosene fuel, e.g. soot reduction and improved fuel efficiency, and which alcohol-enriched Kerosene is the total finished blended fuel product, in accordance with an embodiment of the invention.
Figure 11:
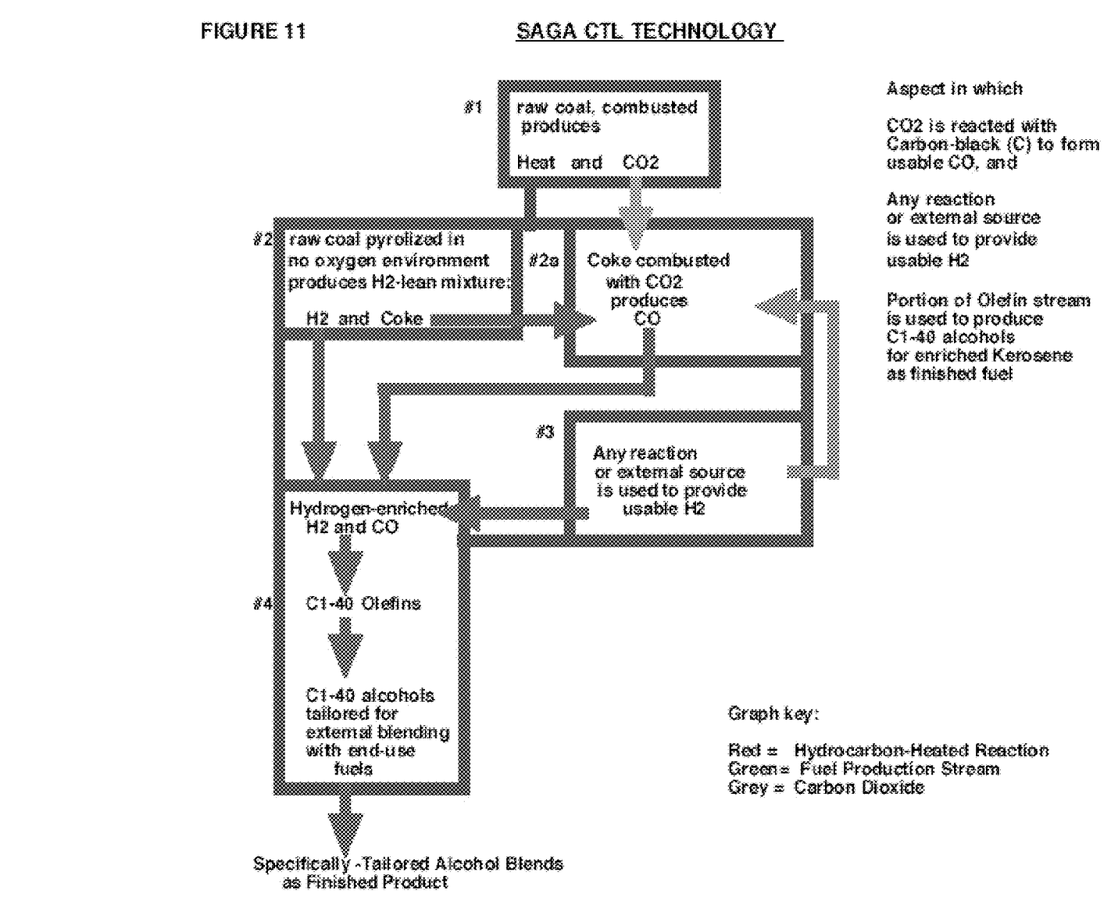
FIG. 11 shows a coal-to-liquid process in which any reaction or external source is used to provide usable Hydrogen ($H_2$), and a portion of the Olefin stream is re-directed to produce C1-40 Alcohols, which Alcohols are tailored for blending with Kerosene or Gasoline, Diesel Fuel or Jet Fuel, Heating Oil, Marine Fuel, Heavier Distillate Fuels or Bunker Fuels and are shipped as the final blended fuel products to an external source for blending with Kerosene, Gasoline, Diesel Fuel, Jet fuel, Heating Oil, Marine Fuel, Heavier Distillate Fuels or Bunker Fuels to improve combustion characteristics of the total externally-marketed generally-fossil-derived finished fuels, in accordance with an embodiment of the invention.

With continued reference to FIG. 8, in a third reaction (Reaction 3), the $CO_2$ formed in the first reaction and the Carbon provided by the second reaction are directed to a reaction chamber for reacting $CO_2$ with Carbon to form CO. The CO is directed to the fuels production process (see below).

Next, in a fourth reaction (Reaction 4), CO is combined with the first and second $H_2$ products, and this combined CO and $H_2$ are reacted in a fuels production process to form one or more alkenes, $CH_2=CH(CH_2)_nCH_3$, wherein 'n' is an integer greater than or equal to 1. At least a portion of the alkenes can be converted to alcohols. Next, in a fifth reaction (Reaction 5), at least a fraction of the one or more alkenes is reduced to one or more alkanes, $CH_3(CH_2)_mCH_3$, wherein 'm' is an integer greater than or equal to 1. The integer 'm' can be tailored to particular applications. For instance, the one or more alkanes can be tailored for use as jet fuel, diesel fuel, or gasoline.

With continued reference to FIG. 7, the alkanes can be combined with the alkenes, alcohols or combinations thereof to produce a fuel product that can be used to generate electricity. The electricity can be used to power various process elements of the fuels production process, directed to an electricity storage unit, or directed to an electrical grid for distribution.

With reference to FIGS. 7, 8, 9, 10 and 11, in a fourth reaction (Reaction 4) the first and second $H_2$ products and CO from Reaction 2a can be provided to one or more fuel production reactors (or chambers), where the combined $H_2$ product is reacted with CO to form one or more alkenes, $CH_2=CH(CH_2)_nCH_3$, wherein 'n' is an integer greater than or equal to 1. In a preferable embodiment, the one or more alkenes are in liquid form. In an alternative embodiment, a fraction of the one or more alkenes can be converted to one or more alcohols. In an embodiment, the one or more alcohols are in liquid form. The one or more alcohols can include any number of carbon atoms.

In a preferable embodiment, the one or more alcohols can be alcohols having between one and forty carbon atoms. The composition of the one or more alcohols can be tailored to particular applications, such as, e.g., for use with diesel fuel, jet fuel, or gasoline. In an embodiment, alcohols having a lower carbon content work to oxygenate diesel fuel for much better burning; alcohols with a higher carbon content can work as high-quality, readily burning surfactants drawing more hydrophilic, lighter alcohols into the oleophyllic host diesel fuel.

With continued reference to FIGS. 7, 8, 9,10 and 11, in a fifth reaction (Reaction 5), a portion of the one or more alkenes ($CH_2=CH(CH_2)_nCH_3$) can be converted to one or more alkanes, $CH_3(CH_2)_mCH_3$, wherein 'm' is an integer greater than or equal to 1. In an embodiment, the one or more alkanes are in liquid form. In an embodiment, this is achieved by reducing the one or more alkenes with the aid of hydrogen. In an embodiment, the one or more alkanes include kerosene. The composition of the one or more alkanes can be tailored to particular applications, such as, e.g., for use as diesel fuel, jet fuel, or gasoline. For example, if the one or more alkanes are desired for use in diesel fuel, a carbon chain length between about 10 and 18 carbon atoms can be used. As another example, if the one or more alkanes are desired for use in gasoline, a carbon chain length between about 6 and 10 carbon atoms can be used. As still another example, if the one or more alkanes are desired for use in jet fuel, a carbon chain length between about 10 and 14 carbon atoms can be used.

Alcohol-Enriched Fuels Production

In various embodiments, the one or more alkanes ($CH_2=CH(CH_2)_nCH_3$) can be combined with the one or more alcohols to form a fuel blend or mixture. As an example, kerosene can be combined with a mixture of C1-C12 alcohols to form the fuel blend. In one embodiment, if diesel fuel is desired, the composition of the one or more alkanes is tailored for diesel fuel use, the composition of the one or more alcohols is tailored for diesel fuel use, and the fuel blend is formed from the individual compositions tailored for diesel fuel use.

In embodiments, the fuel blend can be directed to an electricity generator. The electricity generator can be configured for use with diesel fuel. The fuel blend is combusted to generate electricity. In an embodiment, at least a portion of the electricity produced by the electricity generator is used to dissociate $H_2O$ into $H_2$ and $O_2$ (Reaction 3, FIG. 7). In an embodiment, a portion of the electricity produced by the electricity generator is directed to an electricity storage unit, a power grid (e.g., external power grid), or both.

With reference to FIG. 7, by-product $CO_2$ formed from the combustion of the fuel blend during the generation of electricity can be reduced to CO. In an embodiment, the $CO_2$ produced from the electricity generator is provided as input to Reaction 2a.

In a preferable embodiment, the fuel blend can be compositionally tailored to provide for cleaner burning of the components of the fuel blend with oxygen during the generation of electricity. $CO_2$ formed during the generation of electricity can be reduced to CO, which can be recycled to the one or more fuel production reactors for reaction with $H_2$ to form one or more alkenes.

In such a case, any additional electricity formed upon the combustion of the fuel blend in the electricity generator, for example—can be provided to an electricity storage unit, an external electric (or electricity) grid, or both.

With reference to FIGS. 6 and 7, in an embodiment, at least a portion of the electricity produced from steam-turbine-generated electricity or from combusting the fuel blend in an electricity generator can be used to convert coal (also "raw coal" herein) into $H_2$ and carbon, per Reaction 1. In an embodiment, the electricity can be used to provide resistive heating to a reaction vessel (furnace) to react raw coal in a no-oxygen environment to produce $H_2$ and Carbon. This can reduce the need to combust coal to generate heat energy. With continued reference to FIGS. 6 and 7, any carbon formed in Reaction 2 can be reacted with $CO_2$ to form CO, per Reaction 2a. Next, the $H_2$ produced from coal in Reaction 2 can be augmented with $H_2$ from $H_2O$ electrolysis in a third reaction (Reaction 3). In an embodiment, electricity for the electrolysis of $H_2O$ can be provided from a steam-turbine or electricity generator (see below). In a fourth reaction (Reaction 4), the $H_2$ formed in Reactions 2 and 3 and the CO formed in Reaction 2a can be combined. With continued reference to FIGS. 6 and 7, the CO formed in Reaction 2a and $H_2$ formed in Reactions 2 and 3 are reacted in one or more fuels production process, to form one or more alkenes, $CH_2\!=\!CH(CH_2)_nCH_3$, wherein 'n' is an integer greater than or equal to 1. At least a portion of the alkenes can be converted to alcohols. Next, in a fourth reaction (Reaction 4), at least a fraction of the one or more alkenes is reduced to one or more alkanes, $CH_3(CH_2)_mCH_3$, wherein 'm' is an integer greater than or equal to 1. The integer 'm' can be tailored to particular applications. For instance, the one or more alkenes can be converted to alcohols ranging in carbon length from C1-40, and the one or more alkanes can be tailored for use as jet fuel, diesel fuel, or gasoline.

Next, a fuel blend can be prepared with at least a portion of the alkanes. In some embodiments, the fuel blend can include one or more of the alkanes formed in Reaction 4 and the alcohols formed from the alkenes. In an embodiment, at least a portion of the fuel blend can be stored for use as a saleable product.

With continued reference to FIG. 7, in an embodiment, the fuel blend is combusted in an electricity generator to generate electricity. The electricity can be used in the electrolysis of $H_2O$, per Reaction 3. The electricity can also be used to augment the conversion of coal into $H_2$ and carbon, per Reaction 2. In an embodiment, the electricity can be directed to an energy storage unit, a power grid (e.g., external power grid), or both. Any $O_2$ produced from the electrolysis of $H_2O$ can be re-directed for improved combustion reactions within the fuels production system.

Various reactions of embodiments of the invention can occur in one or more reactors or reaction chambers. For example, Reaction (or Step) 1 and Reaction 2 of FIGS. 2-11 can take place sequentially in a single fuel production reaction chamber. As another example, Reaction 2 and Reaction 2a of FIGS. 2-11 can take place sequentially in a single fuel production reaction chamber. As an alternative, Reaction 2 and Reaction 2A of FIGS. 2-11 can take place in a plurality of reaction chambers.

It will be appreciated that the electricity generator of various embodiments of the invention can be any generator configured to produce electricity. In some cases, the electricity generator produces electricity via the combustion of fuel in the presence of an oxidizing agent, such as oxygen ($O_2$). In such a case, the electricity generator can be a diesel engine generator. In other cases, the electricity generator can be a turbine, such as a steam turbine. If a steam turbine is desired, heat produced via the fuels production processes of embodiments of the invention can be used to generate steam in a boiler or a heat exchanger that is in fluid communication with the steam turbine.

Fuel blends of preferable embodiments of the invention can comprise one or more of alkenes, alkanes and alcohols. In various embodiments, the fuel blend is formed from alkanes, alkenes and alcohols produced at various stages of fuels production processes of various embodiments of the invention.

While preferable embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein can be employed in practicing the invention. It is intended that the following claims define the scope of the invention and that methods and structures within the scope of these claims and their equivalents be covered thereby.

What is claimed is:

1. A method for converting a carbon based compound to fuel, comprising:
    generating heat from a carbon based compound;
    using the heat to generate electricity and carbon dioxide ($CO_2$);
    generating a first product hydrogen ($H_2$) and carbon black or coke (C) from the carbon based compound;
    re-circulating carbon dioxide ($CO_2$) to react with carbon black or coke (C) to form carbon monoxide (CO);
    generating a second product hydrogen ($H_2$); and
    reacting carbon monoxide (CO) with the first and second product hydrogen ($H_2$) to form liquid hydrocarbon.

2. The method of claim 1, wherein the second product $H_2$ is generated by reacting carbon monoxide (CO) and water over a metal catalyst.

3. The method of claim 1, wherein generating the second product hydrogen ($H_2$) comprises the reaction of natural gas, methane ($CH_4$), with steam to produce hydrogen ($H_2$) and carbon dioxide ($CO_2$).

4. The method of claim 1, wherein generating the second product hydrogen ($H_2$) comprises the reaction of natural gas, methane ($CH_4$) with oxygen ($O_2$) to produce hydrogen ($H_2$) and carbon monoxide (CO).

5. The method of claim 4, wherein the reaction of $CH_4$ with $O_2$ also generates water ($H_2O$).

6. The method of claim 1, wherein generating the second product hydrogen ($H_2$) comprises the dry-reformation of natural gas, methane ($CH_4$) with a catalyst and carbon dioxide (CO2) to produce hydrogen ($H_2$) and carbon monoxide (CO).

7. The method of claim 1, wherein generating the second product Hydrogen ($H_2$) comprises the electrolysis of water.

8. The method of claim 1, wherein electricity is generated from steam-turbines, wherein heat for steam-turbine electricity generation is re-directed from the initial process of generating heat from a carbon based compound.

9. The method of claim 1, wherein the electricity is used in generating the first product hydrogen ($H_2$) and carbon black or coke (C) from the carbon based compound.

10. The method of claim 1, wherein the electricity is used in generating a second hydrogen ($H_2$) product.

11. The method of claim 1, wherein $O_2$ is generated as a by-product of generating a second hydrogen ($H_2$) product, and wherein the $O_2$ is used during generating heat from a carbon based compound.

12. The method of claim 1, wherein generating hydrogen ($H_2$) comprises using any method, including importation of hydrogen ($H_2$) from an external source.

13. The method of claim 1, further comprising converting the liquid hydrocarbon to one or more alcohols ranging in carbon length from C1 to C40.

14. The method of claim 13, wherein the C1 to C40 alcohols are blended with Kerosene, Gasoline, Diesel Fuel and/or Jet Fuel.

15. The method of claim 1, further comprising converting the liquid hydrocarbon to Kerosene, Gasoline, Diesel Fuel and/or Jet Fuel.

16. The method of claim 1, wherein electricity is generated from diesel engine generators that use diesel fuel that is a mixture of liquid hydrocarbons.

\* \* \* \* \*